(12) United States Patent
Hasegawa

(10) Patent No.: US 6,168,582 B1
(45) Date of Patent: Jan. 2, 2001

(54) ABSORBENT ARTICLE WRAPPER COMPRISING A SIDE FLAP FASTENER COVER

(75) Inventor: Maki Hasegawa, Suita (JP)

(73) Assignee: The Procter & Gamble Company, Cincinnati, OH (US)

(*) Notice: Under 35 U.S.C. 154(b), the term of this patent shall be extended for 0 days.

(21) Appl. No.: 09/319,748
(22) PCT Filed: Dec. 12, 1996
(86) PCT No.: PCT/US96/19567
§ 371 Date: Jun. 10, 1999
§ 102(e) Date: Jun. 10, 1999
(87) PCT Pub. No.: WO98/25561
PCT Pub. Date: Jun. 18, 1998

(51) Int. Cl.[7] .............................. A61F 13/15; A61B 17/06
(52) U.S. Cl. .................. 604/385.02; 604/387; 604/389; 206/438
(58) Field of Search ................. 604/385.02, 385.01, 604/385.03, 385.04, 385.05, 386, 387, 389, 390; 206/438, 440

(56) References Cited

U.S. PATENT DOCUMENTS

| | | | |
|---|---|---|---|
| 5,088,993 | * 2/1992 | Gaur | 604/385.02 |
| 5,478,336 | * 12/1995 | Pigneul | 604/385.02 |
| 5,569,228 | * 10/1996 | Byrd et al. | 604/385.02 |
| 5,683,377 | * 11/1997 | Mizutani | 604/385.02 |
| 5,792,131 | * 8/1998 | Mizutani | 604/385.02 |

* cited by examiner

Primary Examiner—Dennis Ruhl
(74) Attorney, Agent, or Firm—Matthew P. Fitzpatrick

(57) ABSTRACT

An individually packaged absorbent article (20) having a pair of first flaps (24) and a pair of second flaps (25) with fasteners, such as adhesive fasteners (76, 77) thereon, is disclosed. The absorbent article is wrapped by a wrapper (78) for individually packaging the absorbent article. The wrapper comprises a main wrapper sheet (80) and a first flap fastener cover (84). Adhesive fasteners of the first flaps are releasably covered by the first flap fastener cover which is joined to a part of the main wrapper sheet. Adhesive fasteners of the second flaps are releasably covered by an outer surface of the main wrapper sheet. The first flap fastener cover protects the fasteners located on the first flaps of the absorbent article and maintains the flaps in a position which protects an absorbent side of the absorbent article from contamination until the article is ready for use. The outer surface of the main wrapper sheet protects the fasteners located on the second flaps of the absorbent article and maintains the flaps in a position which protects an absorbent side of the absorbent article from contamination until the article is ready for use. The main wrapper sheet overlays one major surface of the absorbent article and by folding the article and sealing the wrapper in that folded orientation, an individually packaged disposable absorbent article is provided.

10 Claims, 8 Drawing Sheets

ABSORBENT ARTICLE WRAPPER COMPRISING A SIDE FLAP FASTENER COVER

FIELD OF INVENTION

This invention relates to an absorbent article individually packaged by a wrapper comprising a main wrapper sheet for the absorbent article and a flap fastener cover for flap fasteners of flaps. More particularly, this invention relates to an absorbent article comprising a pair of first flaps and a pair of second flaps apart from the first flaps in the longitudinal direction, wherein each flap is covered by a main wrapper sheet or a flap fastener cover.

BACKGROUND OF THE INVENTION

An absorbent article such as a sanitary napkin comprising a pair of flaps which extend laterally outward from an absorbent means is well known. One type of such an absorbent article comprises a pair of flaps which extend laterally outward from a central region of both longitudinal side edges of an absorbent means. The flaps are intended to be folded around the edges of a wearer's undergarment in the crotch region. Thus, in use the flaps are disposed between the edges of the wearer's undergarment in the crotch region and the wearer's thighs. Commonly, the flaps are provided with flap fasteners such as adhesive for affixing the flaps to the underside of the wearer's undergarment. The flaps serve at least two purposes. First, the flaps prevent exudates which otherwise would soil the edges of the weaer's undergarment from doing such. Second, the flaps help stabilize the napkin from shifting out of the position chosen by the wearer. This is especially so when the flaps are affixed to the underside of the undergarment.

The flaps of such sanitary napkins may be folded onto the topsheet side or the backsheet side to conserve space during packaging, i.e., the period between manufacture of the sanitary napkin and its intended first use by the wearer. At the time of the first use by the wearer, the flaps are usually unfolded to facilitate installation of the sanitary napkin into the wearer's undergarment. The flap fasteners of the folded flaps are usually covered by a flap fastener cover so as not to inadvertently adhere to each other or another part of the product before the sanitary napkin is used. When the flaps are folded onto the topsheet side, the flap fasteners of the flaps face outside and are covered by the flap fastener cover thereby bridging the flaps to each other over the topsheet. Japanese Laid-open Patent publication H5-293139 published on Nov. 9, 1993, Japanese Laid-open Patent publication H6-78953 published on Mar. 22,1994 and Japanese Laid-open Utility-Model publication H6-26835 published on Apr. 12, 1994 disclose sanitary napkins having flaps which are folded onto the topsheet and flap fasteners which are covered by a flap fastener cover. The sanitary napkins disclosed therein further comprise a main fastener for securing the sanitary napkin to the inside of the wearer's undergarment. The main fastener is also covered by a main fastener cover. Therefore, when the sanitary napkin is used, the wearer must remove both the flap fastener cover and the main fastener cover. The wearer must then properly dispose of the various fastener covers to prevent them from becoming litter.

Attempts to facilitate removal of a flap fastener cover and a main fastener cover from the sanitary napkin have been made. Japanese Laid-open Utility-Model publication H5-9526 published on Feb. 9, 1993 and Japanese Laid-open Utility-Model publication H5-9529 published on Feb. 9, 1993 disclose sanitary napkins comprising a sanitary napkin main body with a main body fastener, flaps with flap fasteners and a fastener cover for covering the flap fasteners and the main fastener. The fastener cover comprises flap fastener cover portions and a main fastener cover portion which are connected to each other. Therefore, as the main fastener cover portions are removed from the sanitary napkin main body, the flap fastener cover portion is also removed from the flaps. This publication, however, does not disclose arrangements for absorbent articles having a wrapper for individually packaging the absorbent article.

Other attempts to facilitate removal of a flap fastener cover and/or a main fastener cover from a sanitary napkin main body have been made in connection with removal of a wrapper for individually packaging the sanitary napkin. Japanese Laid-open Utility-Model publication H6-26833 published on Apr. 12, 1994 discloses a sanitary napkin comprising a sanitary napkin main body with a main fastener, flaps with flap fasteners, a wrapper for packaging the sanitary napkin main body, a flap fastener cover and a main fastener cover. The main fastener cover is connected to a part of the wrapper so that the main fastener cover is removed from the main body as the sanitary napkin main body is taken out from the wrapper. However, the flap fastener cover also must be removed from the flaps.

Japanese Laid-open Utility-Model H7-39820 published on Jul. 18, 1995 discloses a sanitary napkin comprising a sanitary napkin main body having a topsheet, a backsheet, and an absorbent core. The sanitary napkin also comprises a pair of flaps which are folded around the edges of a wearer's undergarment in the crotch region when the sanitary napkin is used. Adhesive layers provided with the main body and the flaps are covered by an adhesive layer cover which may comprise a wrapper for individually packaging the sanitary napkin. The flaps are folded to the inside of the main body. The adhesive layer cover covering the adhesive layers of the main body extends beyond the longitudinal sides and transverse edges of the main body. The adhesive layer cover extends beyond one transverse end and the extending portion of the adhesive layer cover is folded toward the inside to cover the adhesive layers of the flaps. Japanese Laid-open Utility-Model H6-75446 published on Jul. 18, 1995 discloses a sanitary napkin comprising a sanitary napkin main body and a pair of flaps extending laterally outward from the both sides in the longitudinal direction of the sanitary napkin. The flaps are folded onto a body facing side of the sanitary napkin before the sanitary napkin is used, and are folded around the edges of a wearer's undergarment in the crotch region when the sanitary napkin is used. A garment facing side of the sanitary napkin provided with an adhesive layer is wrapped by a wrapper releasably treated. The wrapped sanitary napkin is folded together with the wrapper about a folding line. This publication further discloses a packaging structure for the sanitary napkin where a part of the wrapper covers the adhesive layers of the flaps. Namely, the transverse edge of the wrapper extends beyond the end edge of the sanitary napkin and is folded towards the adhesive layers of the flaps which are folded onto the topsheet. These publications, however, do not disclose arrangements for absorbent articles having another pair of flaps apart from the flaps in the longitudinal direction of the absorbent article.

Another type of an absorbent article comprises a pair of flaps which extend laterally outward from a back region of both longitudinal side edges of an absorbent means. The flaps of the second type of an absorbent article are intended to stay widespread in a back region of the inside of a wearer's undergarment. In use, the flaps are disposed between the wearer's hips and the wearer's undergarment. The flaps of the second type of an absorbent article also prevent exudates which otherwise would soil the back region of the wearer's undergarment. The flaps may be provided with flap fasteners such as adhesive for affixing the flaps to the inside of the wearer's undergarment to stabilize the napkin shifting in the back region of the wearer's undergarment. The flap fasteners may be covered by a flap fastener cover not to inadvertently adhere to each other or another part of the product before the sanitary napkin is used. Japanese Laid-open Patent publication H8-224269 published on Sep. 3, 1996 discloses an individually packaged sanitary napkin. The sanitary napkin comprises a topsheet, a backsheet, an absorbent core, a pair of back flap portions having adhesive layers on both back sides in the longitudinal direction of the sanitary napkin, and a main adhesive layer covered by a main release paper. The back flap portions are folded onto the topsheet side so that the adhesive layers of the back flap portions face upwardly and a flap release paper is attached on the adhesive layers. A wrapper is joined to the non-releasably treated surface of the main release paper by using a first adhesive. The sanitary napkin is folded into three regions together with the wrapper so that the flap release paper faces the backsheet side of the front portion of the sanitary napkin. The wrapper covering the front portion of the sanitary napkin is joined to the non-releasably treated surface of the flap release paper by using a second adhesive. This publication, however, does not disclose arrangements for absorbent articles having another pair of flaps apart from the flaps in the longitudinal direction of the absorbent article.

While prior art absorbent articles such as sanitary napkins have addressed some of the problems of achieving an individually packaged absorbent article, they have not addressed the problems to the extent of or in the manner of the present invention. Therefore, a primary object of the present invention is to provide an improved individually packaged absorbent article.

SUMMARY OF THE INVENTION

The present invention provides an individually packaged absorbent article comprising: (a) an absorbent article extending in a longitudinal direction and comprising a main body portion having a pair of longitudinal side edges, a pair of end edges, a garment surface, and a body surface, wherein the garment surface of the main body portion may be placed in a wearer's undergarment, and the absorbent article comprises a pair of first flaps joined to the main body portion and extending laterally outward beyond a longitudinal side edge of the main body portion and a pair of second flaps joined to the main body portion apart from the first flaps in the longitudinal direction and extending laterally outward beyond a longitudinal side edge of the main body portion, wherein the garment surface of each of the first and second flaps comprises a first flap fastener and a second flap fastener respectively, and the first and second flaps are folded over the body surface of the main body portion to expose the flap fasteners; (b) a wrapper for the absorbent article, the wrapper comprising a main wrapper sheet and a first flap fastener cover, wherein (c) the main wrapper sheet comprising a pair of longitudinal side portions, a pair of end portions, an inner surface facing the main body portion and an outer surface, the main wrapper sheet is positioned adjacent to the garment surface of the main body portion, wherein the main wrapper sheet and the main body portion of the absorbent article comprises at least two transverse axes and at least three regions divided by the two axes, wherein the three regions comprise a first region into which a majority of the first flaps extend, a second region into which a majority of the second flaps extend and a third region, (d) the first flap fastener cover is joined to at least a part of the main wrapper sheet of the third region, wherein (e) the main wrapper sheet and the main body portion of the absorbent article are folded as a unit about one axis of the two axes so that the majority of the first flaps faces the main body portion of the third region, and the first flap fastener cover is releasably affixed to the first flap fasteners, and (f) the main wrapper sheet and the main body portion of the absorbent article are folded as a unit about the other axis of the two axes so that the majority of the second flaps faces the outer surface of the main wrapper sheet, and the second flap fasteners of the second flaps are releasably affixed to the outer surface of the main wrapper sheet.

DETAILED DESCRIPTION OF THE INVENTION

Figure 1:
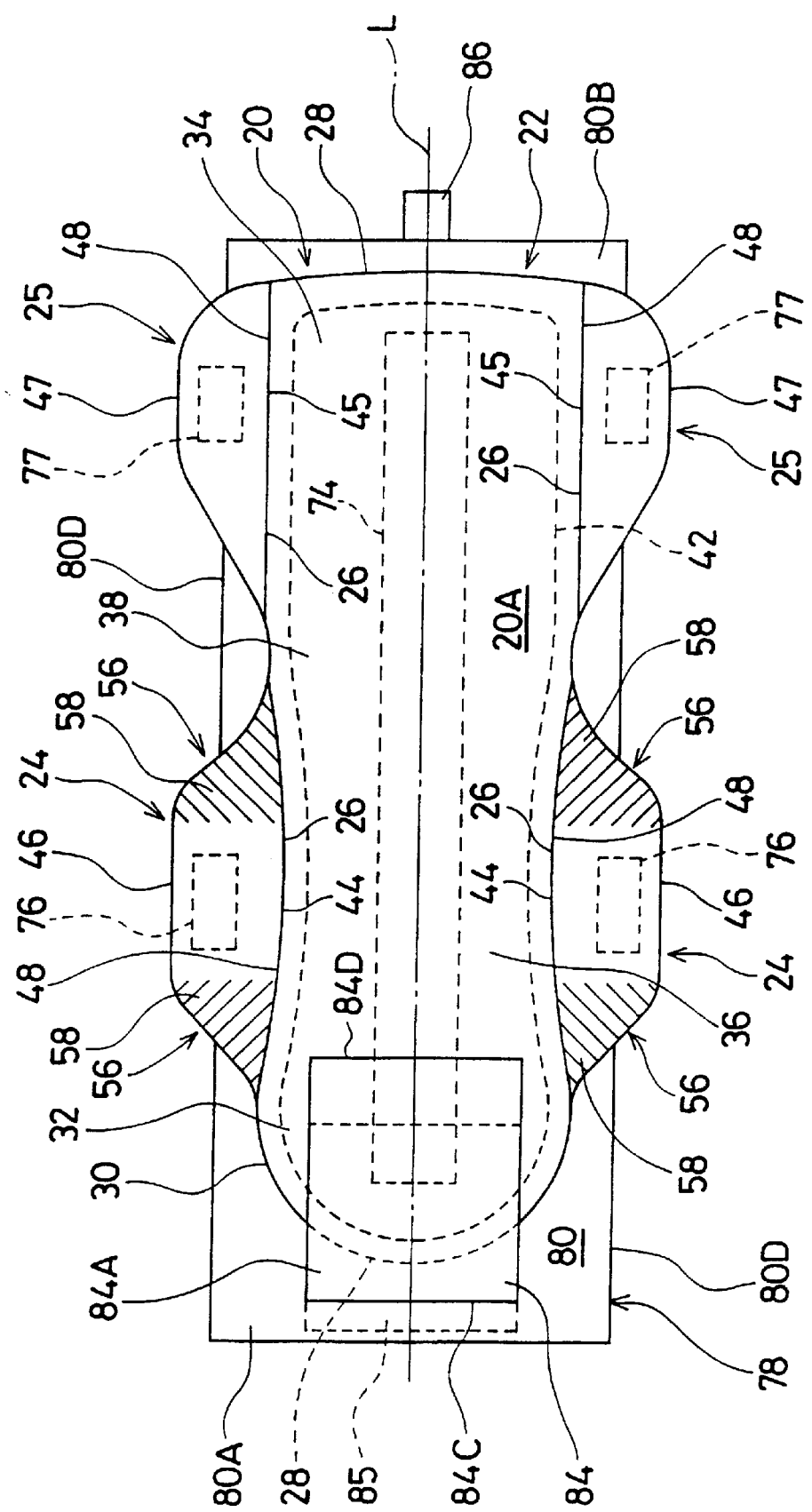
FIG. 1 is a top plan view of a preferred embodiment of the wrapper of the present invention in an opened position with a preferred sanitary napkin disposed thereon and the flaps of the sanitary napkin outstretched.
Figure 2:
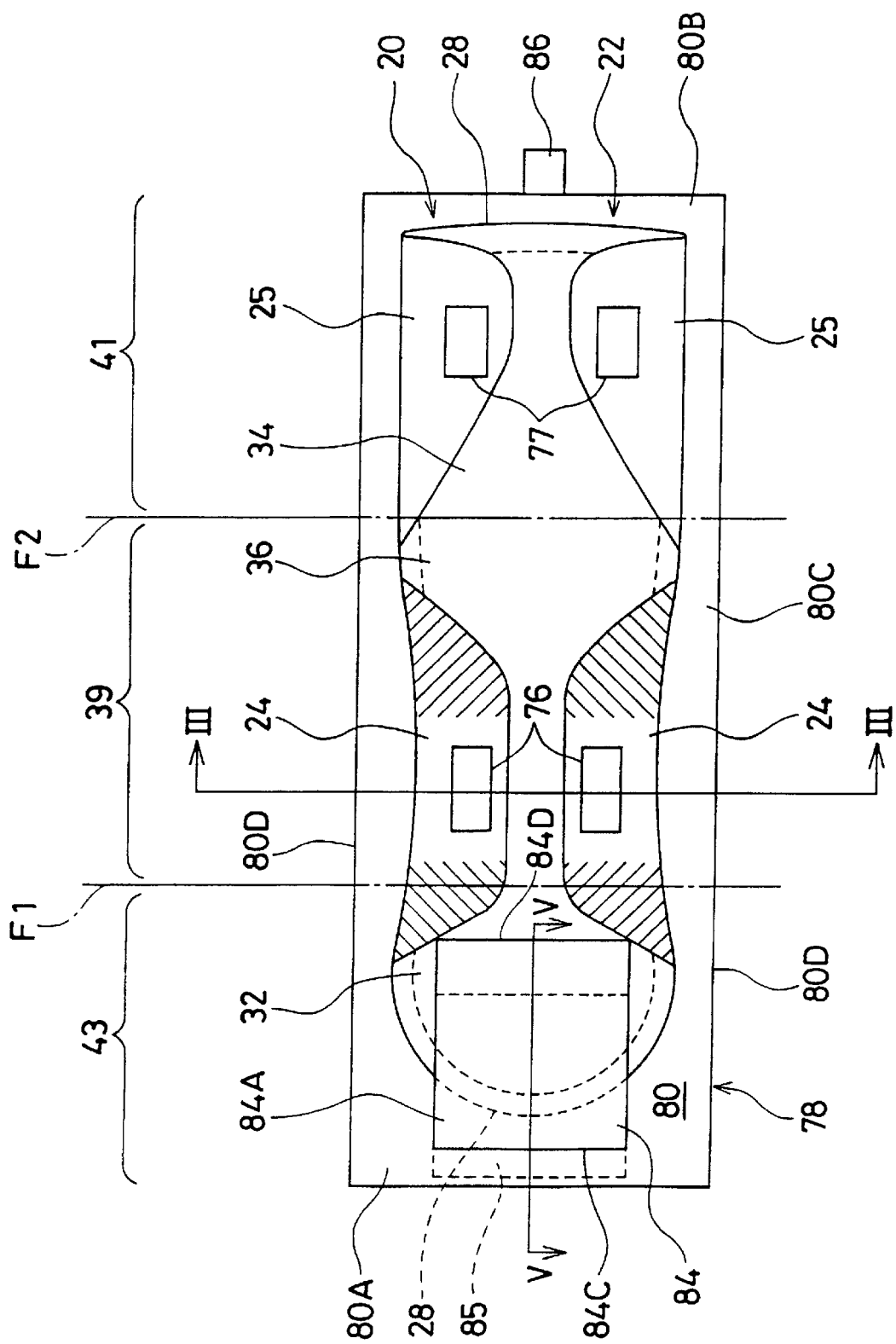
FIG. 2 is a top plan view of the wrapper of the present invention shown in FIG. 1 with the flaps of the sanitary napkin folded over the topsheet.
Figure 3:
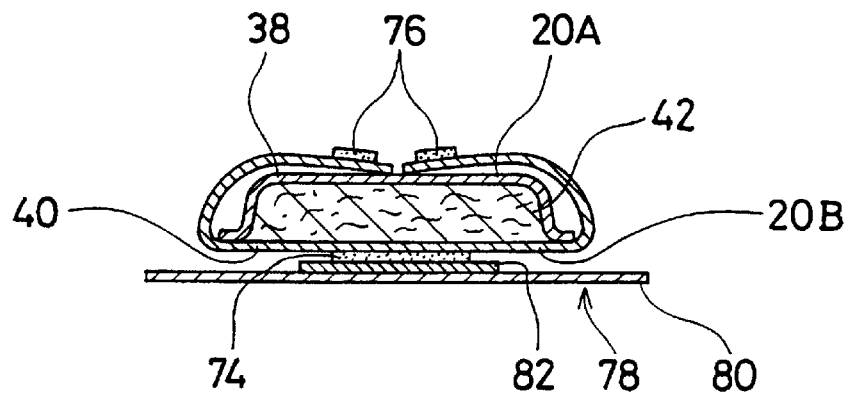
FIG. 3 is a cross-sectional view of FIG. 2 taken along the line III—III.

Referring now to the drawings, the present invention is embodied in a preferred but non-limiting embodiment. As shown in FIGS. 1, 2, and 3, the invention comprises a wrapper 78 for a disposable absorbent article, particularly a sanitary napkin 20.

The sanitary napkin 20 is used to collect vaginal discharges, such as menses, and prevent soiling of the wearer's clothing by such discharges. As shown in FIGS. 1 and 2, the sanitary napkin 20 basically comprises a main body portion 22 and first flaps 24 and second flaps 25. The main body portion 22 of the sanitary napkin 20 may have a fastener, such as a pressure sensitive adhesive fastener 74 thereon for fastening the main body portion 22 in the wearer's undergarment. The first flaps 24 preferably each have first fasteners thereon, such as a pressure sensitive adhesive fastener 76, for releasably affixing the first flaps 24 of the sanitary napkin 20 in a configuration folded around the edges of the crotch of the wearer's undergarment. The second flaps 25 preferably each have second fasteners thereon, such as a pressure sensitive adhesive fastener 77, for releasably affixing the second flaps 25 of the sanitary napkin 20 in a configuration staying widespread in a back region of the inside of a wearer's undergarment. The wrapper 78 of the present invention serves to cover and protect the first flap fasteners 76, the second flap fasteners 77, and the main body fastener 74 (if there is one), and is folded around the sanitary napkin 20 to provide an individual package for the sanitary napkin 20. Before looking at the characteristics of the wrapper 78 in greater detail, the properties of the sanitary napkin 20 will be briefly discussed.

The sanitary napkin 20 (and the main body portion 22 thereof) has two surfaces, a liquid pervious body-contacting surface or "body surface" 20A that is intended to be worn adjacent to the body of the wearer, and a liquid impervious garment surface 20B. The sanitary napkin 20 is shown in FIG. 1 as viewed from its body surface 20A. The sanitary napkin 20 has two centerlines, a principal longitudinal centerline L and a principal transverse centerline (not shown in FIG. 1). The term "longitudinal," as used herein, refers to a line, axis or direction in the plane of the sanitary napkin 20 that is generally aligned with (e.g. approximately parallel to) a vertical plane which bisects a standing wearer into left and right body halves when the sanitary napkin 20 is worn. The terms "transverse," "lateral" or "width" used herein, are interchangeable, and refer to a line, axis or direction which lies within the plane of the sanitary napkin 20 that is generally perpendicular to the longitudinal direction.

FIG. 1 shows that the main body portion 22 of the sanitary napkin 20 comprises the portion of the sanitary napkin without the first flaps 24 and the second flaps 25. The main body portion 22 has two spaced apart longitudinal edges 26, two spaced apart transverse or end edges (or "ends") 28, which together form the periphery 30 of the main body portion. The main body portion 22 also has three sections comprising a central section (first section) 36, one end section (second section) 34 and the other end section (third section) 32. The first section 36 is disposed between the second section 34 and the third section 32. The second section 34 and the third section 32 extend outwardly in the longitudinal direction from the edges of the central region 36 of the main body portion 22. When the sanitary napkin 20 is individually packaged, the main body portion 22 and the wrapper 78 are folded into three regions comprising a first region 39, a second region 41, and a third region 43 divided by two fold axes F1 and F2 (refer to FIG. 2). The first section 36, the second section 34 and the third section 32 of the main body portion 22 generally extend in the first region 39, the second region 41 and the third region 43, respectively.

The main body portion 22 of the sanitary napkin 20 can be of any thickness, including relatively thick, intermediate thickness, relatively thin, or even very thin (or "ultra thin"). An "ultra-thin" sanitary napkin 20 as described in U.S. Pat. Nos. 4,950,264 and 5,009,653 issued to Osborn preferably has a caliper of less than about 3 millimeters. The embodiment of the sanitary napkin 20 shown in the drawings is intended to be an example of a sanitary napkin of an intermediate thickness. The main body portion 22 of the sanitary napkin 20 may also be relatively flexible, so that it is comfortable for the wearer. It should be understood that the sanitary napkin shown is merely one embodiment, and that the wrapper of the present invention is not limited to use with absorbent articles of the type or having the specific configurations shown in the drawings.

FIG. 3 shows the individual components of the main body portion 22 of the sanitary napkin 20. The main body portion 22 of the sanitary napkin 20 preferably comprises at least three primary components. These include a liquid pervious topsheet 38, a liquid impervious backsheet 40, and an absorbent core 42 positioned between the topsheet 38 and the backsheet 40. The topsheet, the backsheet, and the absorbent core may be assembled in a variety of configurations known in the art (including layered or "sandwich" configurations and wrapped or "tube" configurations).

Suitable materials for the components of the main body portion 22, and some of the various configurations in which such components can be assembled are described generally in U.S. Pat. No. 4,321,924, entitled "Bordered Disposable Absorbent Article" issued to Ahr on Mar. 30, 1982; U.S. Pat. No. 4,425,130, entitled "Compound Sanitary Napkin" issued to DesMarais on Jan. 10, 1984; U.S. Pat. No. 4,950,264, entitled "Thin, Flexible Sanitary Napkin" issued to Osborn on Aug. 21,1990: U.S. Pat. No. 5,308,346, entitled "Elasticized Sanitary Napkin" issued to Sneller, et al. on May 3, 1994; and U.S. Pat. No. 5,389,094, entitled "Absorbent Article Having Flaps and Zones of Differential Extensibility" issued to Lavash, et al. on Feb. 14, 1995. The main body portion 22 of the sanitary napkin 20 may also be comprised of one or more extensible components such as those sanitary napkins, and the like described in U.S. patent application Ser. Nos. 07/915,133 and 07/915,284, both filed Jul. 23, 1992, in the name of Osborn, et al. (PCT Publication Nos. WO 93/01785 and 93/01786, both published Feb. 4, 1993).

FIGS. 1–3 show a preferred embodiment of the sanitary napkin 20 assembled in a sandwich construction in which the topsheet 38 and the backsheet 40 have length and width dimensions generally larger than those of the absorbent core 42. The topsheet 38 and the backsheet 40 extend beyond the edges of the absorbent core 42 to form portions of the periphery 30. The topsheet 38 is preferably joined to the body-facing side of the absorbent core 42 and the backsheet 40 is preferably joined to the garment-facing side of the absorbent core 42. The topsheet 38 and backsheet 40 can be joined to the absorbent core 42 in any suitable manner known in the art for this purpose, such as by an open pattern of adhesives. The portions of the topsheet 38 and backsheet 40 that extend beyond the edges of the absorbent core 42 are preferably also joined to each other. These portions of the topsheet 38 and backsheet 40 can also be joined in any suitable manner known in the art. Preferably, in the embodiment shown, these portions of the topsheet 38 and backsheet 40 are joined using adhesives over substantially the entire portions that extend beyond the edges of the absorbent core 42, and a crimp seal around the periphery 30 of the main body portion 22 where the topsheet 38 and backsheet 40 are densified by the application of pressure or heat and pressure.

The sanitary napkin 20 shown in FIGS. 1–3, as discussed above, also comprises a pair of first flaps 24 and a pair of second flaps 25 that are joined to the main body portion 22. The first flaps 24 extend laterally outward beyond the longitudinal side edges 26 of the main body portion 22 from their proximal edges 44 to their distal edges (or "free ends") 46. The first flaps 24 extend laterally outward from at least a part of the first section 36 of the main body portion 22 and majority of the first flaps 24 extends in the first region 39 divided by the fold axes F1 and F2. The second flaps 25 extend laterally outward beyond the longitudinal side edges 26 of the main body portion 22 from their proximal edges 45 to their distal edges (or "free ends") 47. The second flaps 25 are positioned adjacent to one end edge 28 of the main body portion 22 apart from the first flaps 24 in the longitudinal direction of the main body portion 22. The second flaps 25 extend laterally from at least a part of the second section 34 of the main body portion 22 and majority of the second flaps 25 extend in the second region 41 divided by the fold axis F2.

The first flaps 24 and the second flaps 25 can be joined to the main body portion 22 in any suitable manner. The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. Preferably, in the embodiment shown in FIGS. 1–3, the first flaps 24 and the second flaps 25 are integral with the main body portion 22 (that is, the flaps 24 and 25 comprise integral extensions of the backsheet 40. Alternatively, the flaps 24 and 25 may comprise integral extensions of the topsheet 38 and the backsheet 40.).

In other alternative embodiments, the flaps 24 and 25 can comprise one or more separate components that are joined to the garment-facing side of the main body portion 22. Preferably, in such a case, the flaps 24 and 25 each comprise a separate component that is joined to the garment-facing side of the main body portion 22. In such alternative embodiments, the flaps 24 and 25 are preferably otherwise unattached to the garment-facing side of the main body portion 22 of the sanitary napkin 20 between the points where they are attached to the main body portion 22 and the longitudinal side edges 26 of the main body portion 22. The flaps 24 and 25 in these latter embodiments can be joined to the garment-facing side of the main body portion 22 by any suitable attachment mechanism. Suitable attachment mechanisms include, but are not limited to adhesives, and the like. The first flaps 24 and the second flaps 25 may be joined to the main body portion 22 by different attachment method from each other.

The places or regions on the sanitary napkin 20 where the flaps 24 and 25 are joined to (or extend from) the main body portion 22, are referred to herein as "junctures". These regions will typically be longitudinally-oriented (or "longitudinal") junctures, such as lines of juncture 48. These regions can be any of various curved or straight lines, but they are not limited to lines. Thus, the junctures can comprise flanges, strips, intermittent lines, and the like.

The first flaps 24 and the second flaps 25 may be of any configuration desired, with one preferred configuration being shown in FIG. 1. FIG. 1 shows that the first flaps 24 are provided with zones of extensibility (or "zones of differential extensibility") 56 in the front edge and the back edge of each flap 24. The zones of extensibility 56 relieve stresses which are created in the first flaps 24 by the folding of the first flaps 24 around the crotch of the wearer's undergarment. The zones of extensibility 56 thereby help eliminate bunching of the first flaps 24 caused by said stresses. Preferably, in the embodiment shown in FIG. 1, the zones of extensibility 56 comprise pre-corrugated or "ring rolled" regions of the first flaps 24 in which the corrugations 58 define ridges and valleys that are oriented at an angle to the principal longitudinal centerline L. Suitable structures for providing the flaps 24 with zones of extensibility 56 are described in greater detail in U.S. Pat. No. 5,389,094 issued to Lavash, et al. and in commonly assigned copending U.S. patent application Ser. No. 08/380,769, entitled "Absorbent Article Having Flaps With Gathered Portions" filed in the name of Sue A. Mills, et al. on Jan. 30, 1995.

The sanitary napkin 20 preferably also has fasteners for securing the sanitary napkin 20 in place in a wearer's undergarment. FIGS. 1 and 2 show a preferred arrangement of fasteners which comprises a main body portion (or central pad) fastener, such as central pad adhesive 74, and flap fasteners, such as first flap adhesives 76 and second flap adhesives 77. The fasteners used with the sanitary napkin 20 are not limited to adhesive fasteners. Any suitable type of fastener known in the art can be used for this purpose. For example, the sanitary napkin 20 could be secured in place in a wearer's undergarment by mechanical fasteners, such as VELCRO®, or by a combination of adhesive and mechanical fasteners. For simplicity, however, the fasteners will be described in terms of adhesive fasteners and these fasteners are preferably pressure sensitive adhesive fasteners. Suitable pressure sensitive adhesive fasteners are described in greater detail in U.S. Pat. No. 4,917,697.

The central pad adhesive 74, the first flap adhesives 76 and the second flap adhesives 77 can be provided in any suitable configuration. In the preferred embodiment shown, the central pad adhesive 74 is provided in the form of a longitudinally oriented strip of adhesive that is centered about the principal longitudinal centerline L. The first flap adhesives 76 and the second flap adhesives 77 are provided in the form of a generally rectangular patch of adhesive on each first flap 24 and each second flap 25 respectively. The central pad adhesive 74 provides an adhesive attachment means for securing the main body portion 22 of the sanitary napkin 20 in the crotch portion of a panty. The first flap adhesives 76 are used to assist in maintaining the first flaps 24 in position after they are wrapped around the edges of the crotch portion of the panty. The second flap adhesives 77 are used to assist in maintaining the second flaps 25 in position after they are rendered widespread in a back region of the inside of the panty. The flaps can be maintained in position by attaching the flaps 24 to the undergarment, or to the opposing flap.

FIGS. 1–3 and 5–6 show one preferred version of the wrapper 78 of the present invention. As shown in FIG. 1, the wrapper, generally designated by reference number 78 comprises several elements. These elements can comprise integral portions of a single member or article, or they can comprise separate components joined to a member or article. The elements comprising the wrapper 78 include: a main wrapper sheet 80; an optional release component, such as a release paper (or release coating) 82 disposed on one side of the main wrapper sheet 80; a first flap fastener cover, such as a first flap adhesive cover 84; a second flap fastener cover, such as a second flap adhesive cover (or release coating) 85. The first flap adhesive cover 84 and the second flap adhesive cover 85 may be generally positioned in the third region 43.

The main wrapper sheet 80 (or "wrapper sheet") is the portion of the wrapper 78 which will be folded around the sanitary napkin 20 to provide an individual package for the sanitary napkin 20. The main wrapper sheet 80 preferably covers and is releasably attached to the central pad adhesive 74. The main wrapper sheet 80 preferably has dimensions that are slightly larger than those of the main body portion 22 of the sanitary napkin 20. Preferably, as shown in FIGS. 1 and 2, the main wrapper sheet 80 has longitudinal side portions 80D which extend beyond the longitudinal side edges 26 of the main body portion 22 of the sanitary napkin 20. The main wrapper sheet 80 preferably also has a first end portion 80A and a second end portion 80B which extend beyond the end edges 28 of the main body portion 22 of the sanitary napkin 20. It is recognized, however, that satisfactory protection of sanitary napkin 20 may be afforded by a wrapper which is not larger than the main body portion 22 of the sanitary napkin 20.

The main wrapper sheet 80 can be made from any suitable material. The main wrapper sheet 80 is preferably manufactured from a thin flexible material which is liquid impermeable so that the wrapper 78 will be suitable for wrapping and disposing of a used sanitary napkin 20. For example, polyethylene films have been found to work well.

Figure 6:
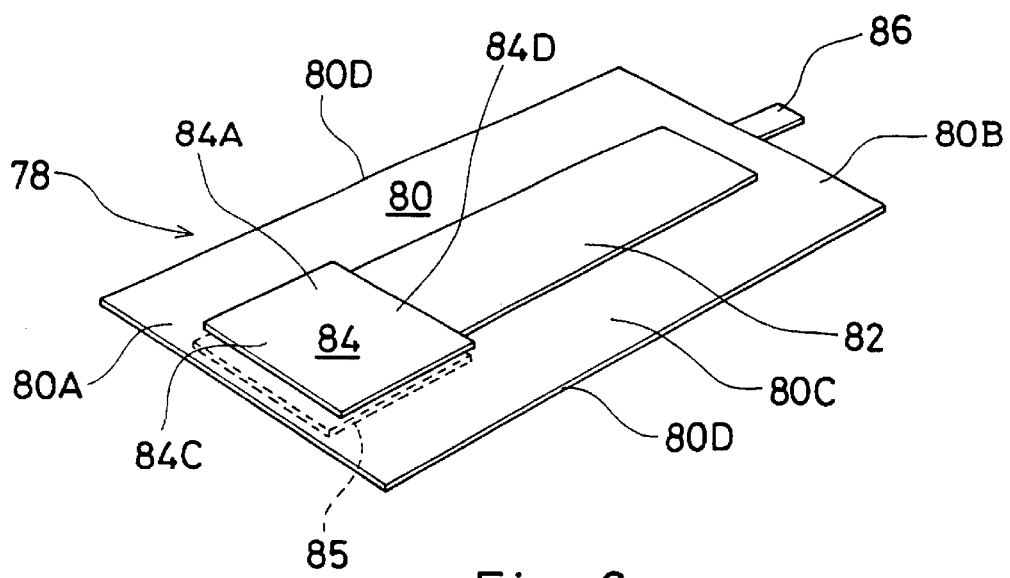
FIG. 6 is a perspective view of one preferred wrapper of the present invention.

The main wrapper sheet 80 can be provided with the optional release component, such as release paper (or release coating) 82 so that the main wrapper sheet 80 will release from the central pad adhesive 74 when the wearer removes the sanitary napkin 20 from the wrapper 78. If a separate release paper is used, it can comprise any suitable material known in the art for this purpose, such as coated papers. Suitable release papers are described in U.S. Pat. No. 4,917,697. Such a release paper 82 can be laminated to the inside surface of the main wrapper sheet 80 as shown in FIGS. 3 and 6. If a release coating is used, the coating can be applied directly to the inside surface of the main wrapper sheet 80. Such a coating can comprise any material known in the art for this purpose, with silicone coatings being preferred. If a coating is used, the coating 82 may be provided by coating only that zone of the main wrapper sheet 80 which will substantially contact the central pad adhesive 76. Alternatively, the entire inside surface of the main wrapper sheet 80 may be coated. Coating the entire inside of a wrapper is disclosed in U.S. Pat. No. 5,181,610 entitled "Flexible Container with Nonstick Interior" which issued to Quick et al. on Jan. 26, 1993.

The first flap adhesive cover (or "flap release strip") 84 covers and protects the first flap adhesives 76 and maintains the first flaps 24 in position folded over the topsheet 38 for packaging. In the preferred embodiment shown in FIGS. 1, 2 and 5, the first flap adhesive cover 84 extends from the first end portion 80A of the main wrapper sheet 80 in the third region 43. The first flap adhesive cover 84 is preferably joined to the main wrapper sheet 80 and biased toward the main wrapper sheet 80 so that it will remain in the configuration shown in FIGS. 1 and 2. As shown in FIGS. 1, 2, 5 and 6, the first flap adhesive cover 84 is joined to the main wrapper sheet 80 at fixed end 84C. The distal end 84D of the first flap adhesive cover 84 extends toward central portion 80C of main wrapper sheet 80 and toward the first section 36 of sanitary napkin 20 (i.e., the first region 39). When the wrapper 78 is in the flat configuration shown in FIG. 1, the first flap adhesive cover 84 lies over the third section 32 of sanitary napkin 20 (i.e., the third region 43). The first flap adhesive cover 84 can be of any suitable size and shape. Although the figures depict a first flap adhesive cover 84 which is only of sufficient width to cover and protect the first flap adhesives 76. A flap adhesive cover 84, which is of a width equal to the width of the main wrapper sheet 80 or any width therebetween is also contemplated herein.

The first flap adhesive cover 84 has two faces, one of which is a non-stick face (or releasable face) 84A, which is capable of releasable attachment with the flap fasteners, and an opposite face or side 84B. Preferably, as shown in FIG. 6, the non-stick face 84A of the first flap adhesive cover 84 faces away from the main wrapper sheet 80 so that it will be able to releasably adhere to the first flap adhesive 76 when the sanitary napkin 20 and the wrapper 78 are in the folded configuration discussed below. When the first flap fasteners 76 comprise adhesive fasteners, the non-stick face 84A can be provided by attaching a separate release paper or element to the first flap adhesive cover 84 which is treated with a non-stick material, or by treating all or a portion of the first flap adhesive cover 84 with a non-stick coating, such as by silicone coating a portion of the first flap adhesive cover 84. Alternatively, if the first flap fasteners 76 comprise mechanical fasteners, such as VELCRO® fasteners, the non-stick face may be provided by a nonwoven material capable of releasably engaging the mechanical fastening material. The opposing side 84B of the first flap adhesive cover 84 need not have, and preferably does not have, a release coating thereon. The opposing side 84B need not have a release coating since it will only be in contact with the topsheet 38 in first end region 32 of sanitary napkin 20 (i.e., the third region) when the sanitary napkin 20 is disposed on wrapper 78 and placed in the folded configuration. In the embodiment shown in FIG. 5, the opposing side 84B which does not have a release coating is joined to the main wrapper sheet 80 at fixed end 84C by applying adhesive layer 83.

Figure 8:
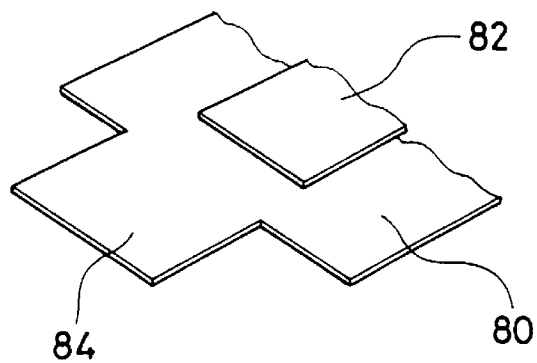
FIG. 8 is a fragmented perspective view of an alternative embodiment of the wrapper of the present invention.

FIG. 8 shows a variation of the first flap adhesive cover 84 shown in the preceding drawing figures. In the embodiment shown in FIG. 8, instead of being a separate component of the main wrapper sheet 80, the first flap adhesive cover 84 is an integral portion of the main wrapper sheet 80.

Figure 5:
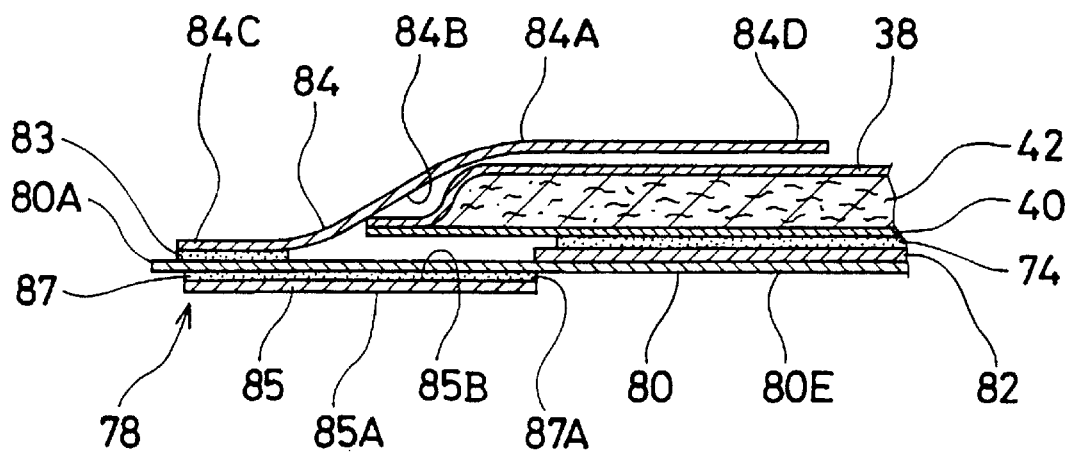
FIG. 5 is a cross-sectional view of FIG. 2 taken along the line V—V.

The second flap adhesive cover (or "flap release strip") 85 covers and protects the second flap adhesives 77 and maintains the second flaps 25 in position folded over the topsheet 38 for packaging. In the preferred embodiment shown in FIGS. 1, 2, 5 and 6, the second flap adhesive cover 85 extends in the third region 43 and is joined to outer surface 80E of the main wrapper sheet 80. The figures depict a second flap adhesive cover 85 which is only of sufficient width to cover and protect the second flap adhesives 77. However, a second flap adhesive cover 85, which is of a width equal to the width of the main wrapper sheet 80 or any width therebetween is also contemplated herein. The second flap adhesive cover 85 has two faces, one of which is a non-stick face (or releasable face) 85A, which is capable of releasable attachment with the flap fasteners, and an opposite face or side 85B. Preferably, as shown in FIG. 5, the non-stick face 85A of the second flap adhesive cover 85 faces away from the outer surface 80E of the main wrapper sheet 80 so that it will be able to releasably adhere to the second flap adhesive 77 when the sanitary napkin 20 and the wrapper 78 are in the folded configuration discussed below. When the second flap fasteners 77 comprise adhesive fasteners, the non-stick face 85A can be provided by attaching a separate release paper or element to the second flap adhesive cover 85 which is treated with a non-stick material, or by treating all or a portion of the second flap adhesive cover 85 with a non-stick coating, such as by silicone coating a portion of the second flap adhesive cover 85. Alternatively, if the second flap fasteners 77 comprise mechanical fasteners, such as VELCRO® fasteners, the non-stick face may be provided by a nonwoven material capable of releasably engaging the mechanical fastening material. The opposing side 85B of the second flap adhesive cover 85 need not have, and preferably does not have, a release coating thereon. In the embodiment shown in FIG. 5, the opposing side 85B which does not have a release coating is joined to the outer surface 80E by applying adhesive layer 87. Alternatively, the area of the outer surface 80E of the main wrapper sheet 80 corresponding to the second flap fastener cover 85 may be releasably treated with a non-stick coating, such as silicone.

The wrapper 78 preferably also comprises an optional package fastener 86 for retaining the package formed by folding the wrapper and sanitary napkin in its folded configuration. The package fastener 86 is preferably both releasably attachable to the package and resealable. The package fastener 86 may be comprised of any releasably attachable and resealable fastener known in the art, such as spots or patches of adhesive, tapes, and mechanical fasteners. A tape tab with a pressure sensitive adhesive located thereon has been found to work well. The package fastener 86 can be disposed at any suitable location on the wrapper 78. In the embodiment shown in FIGS. 1 and 2, the package fastener 86 is preferably positioned at opposing second end portion 80B of the main wrapper sheet 80.

Figure 4:
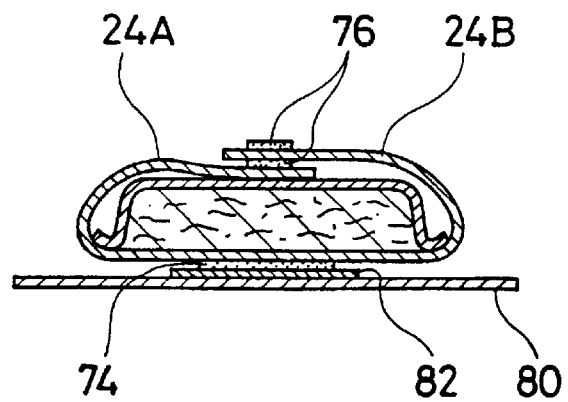
FIG. 4 is a cross-sectional view of an alternate embodiment of the flaps of the sanitary napkin in an alternative topsheet protecting position.

For the initial packaging of the sanitary napkin 20 in the wrapper 78, the garment-facing side 20B of the main body portion 22 is placed on top of the main wrapper sheet 80. The sanitary napkin 20 is positioned so that the central pad fastener 74 lies over the release paper or release coating 82 on the main wrapper sheet 80. The first flaps 24 and the second flaps 25 are then preferably folded over the topsheet 38 so that the first flaps 24 and the second flaps 25 are in the configuration shown in FIGS. 2 and 3. Folding the flaps 24 and 25 in the configuration shown in FIGS. 2 and 3 exposes the patches of adhesive 76 and 77 disposed on the garment-facing side of flaps 24 and 25 and causes the flaps 24 and 25 to cover at least a portion of the topsheet 38. Folding the flaps 24 and 25 over the topsheet 38 can, thus, be considered to provide a degree of protection to prevent the topsheet 38 from becoming soiled prior to use. In alternative embodiments, where one or both of the first flaps 24 has a greater span (that is, its dimension measured in the transverse direction), the first flaps 24 can be folded over the topsheet 38 so that one of the first flaps 24 at least partially overlays the other flap 24 as shown in FIG. 4. The first flap 24B overlays, attaches to, and protects the flap attachment means 76 of the first flap 24A. The flap adhesive cover 84 will then overlay, attach to and protect the flap fastener 76 of the first flap 24B. The second flaps 25 may have the same structure as the first flaps 24 that have a greater span.

After folding the flaps 24 and 25 over the topsheet 38, the sanitary napkin 20 and main wrapper sheet 80 will then preferably be folded into three regions that are defined by the fold axes F1 and F2 shown in FIG. 2. The fold axes F1 and F2 will divide both the sanitary napkin 20 and the main wrapper sheet 80 into three regions comprising the first region 39, the second region 41 and the third region 43. As shown in FIG. 2, the central region (the first region) 39 lies between preferred fold axes F1 and F2. The second and third regions 41 and 43 lie longitudinally outboard of the fold axes F1 and F2. As described above, the main body portion 22 is also separated at the fold axes F1 and F2 into three sections comprising the first section 36, the second section 34, and the third section 32. Each section 36, 34 and 32 generally extends in each region 39, 41 and 43 respectively.

Figure 9:
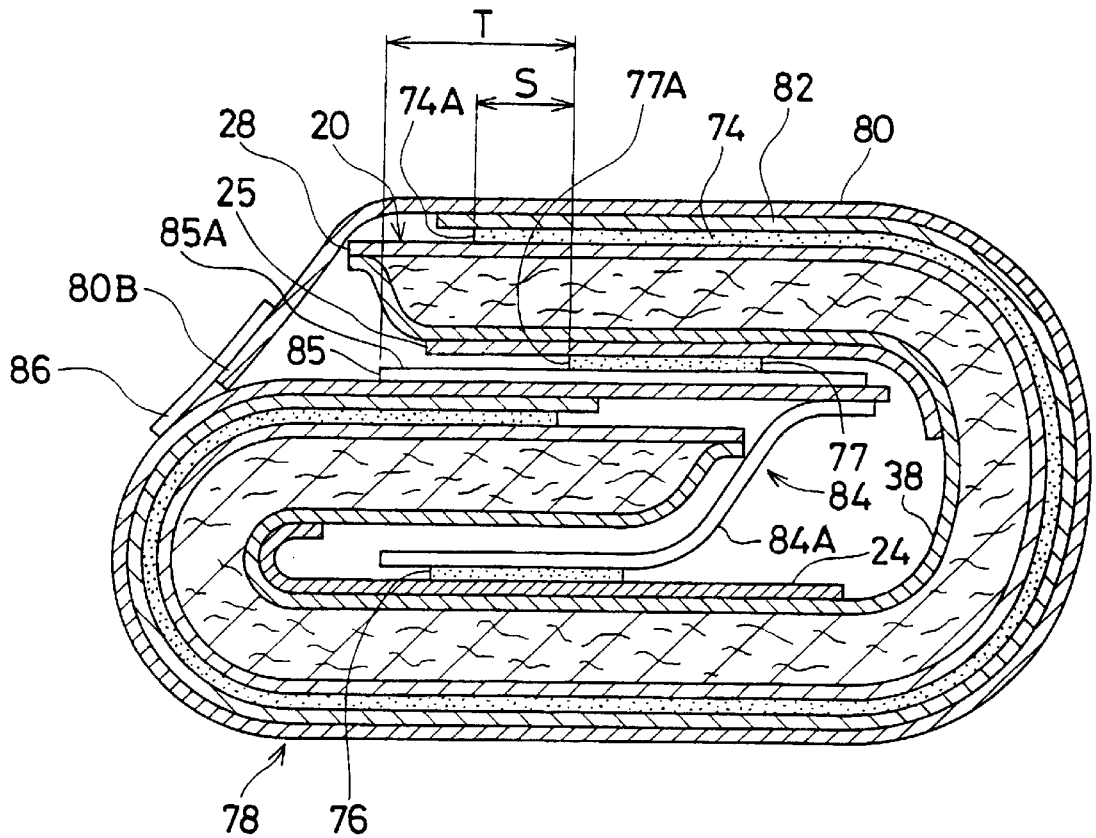
FIG. 9 is a cross-sectional view (taken along the longitudinal centerline) of one preferred wrapper of the present invention with a sanitary napkin therein in a folded configuration.

FIG. 9 depicts the package for the sanitary napkin formed by folding the wrapper 78 and sanitary napkin 20 in one preferred configuration for shipment, sale, and convenient carrying by the wearer. As shown in FIG. 9, the third region 43 (i.e., the first end portion 80A of the main wrapper 80, along with the third section 32 of the main body portion 22, the first flap adhesive cover 84 and the second flap adhesive cover 85) is folded about the fold axis F1 onto the first region 39 (i.e., the first flap adhesive 76 of the first flaps 24, the first section 36 of the main body portion 22 and the central portion 80C of the main wrapper 80). When the sanitary napkin 20 and wrapper 78 are folded in this manner, the non-stick face 84A of the first flap adhesive cover 84 is placed over the first flap fasteners 76 and is releasably attached to each adhesive patch 76. In addition, the first flap adhesive cover 84 provides a connection between each flap 24 that spans the flaps 24, thereby keeping the first flaps 24 in the desired position until the first flap adhesive cover 84 is removed. The second region 41 (i.e., the second end portion 80B of the main wrapper 80, along with the second section 34 of the main body portion, and the second flap adhesive 77 of the second flaps 25) is then folded about the fold axis F2 onto the third region 43 (i.e., the outer surface 80E of the main wrapper sheet 80). When the sanitary napkin 20 and wrapper 78 are folded in this manner, the non-stick face 85A of the second flap adhesive cover 85 is placed over the second flap fasteners 77 and is releasably attached to each adhesive patch 77. By pressing the tape tab 86 onto the exterior of wrapper 78 in the position depicted in FIG. 9, the sanitary napkin 20, its flaps 24 and wrapper 78 remain in the configuration shown.

In a preferred embodiment shown in FIG. 9, the edge 74A of the central pad adhesive 74 in the third region 41 may extend adjacent to the end edge 28 of the main body portion 22 beyond the edge 77A of the second flap adhesive 77 at a distance S. When the second region 41 is folded onto the third region 43 as shown in FIG. 9, the edge 87A (refer to FIG. 5) of the adhesive layer 87 may extend adjacent to the second end portion 80B of the main wrapper sheet 80 beyond the edge 77A of the second flap adhesive 77 at a distance T. The adhesive layer 87 attaches the second flap adhesive cover 85 to the main wrapper sheet 80.

Figure 10:
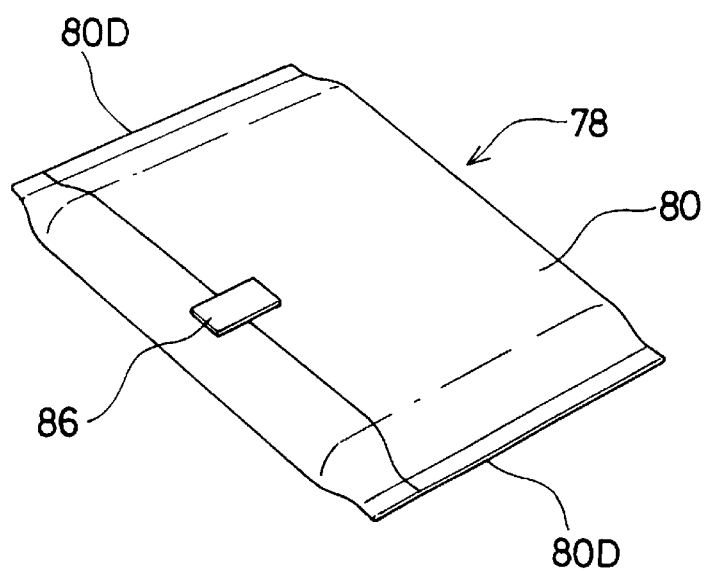
FIG. 10 is a perspective view of one preferred individually packaged absorbent article of the present invention.

Preferably, to complete the individual packaging of the sanitary napkin 20 in the wrapper 78 of the present invention, each longitudinal side edge 80D of the main wrapper sheet 80 is then frangibly sealed after the sanitary napkin 20 and the wrapper 78 are in the folded configuration shown in FIG. 9. The frangible sealing of the side edges 80D of the main wrapper sheet 80 can be accomplished by any suitable sealing technique. By way of example only, the longitudinal side edges 80D may be heat sealed, glued, or ultrasonically bonded as shown in FIG. 10. The entire sanitary napkin 20 is thereby protected until the wrapper 78 is opened. Suitable methods for frangibly sealing the longitudinal side edges are described in U.S. Pat. No. 4,556,146 issued to Swanson.

Figure 11:
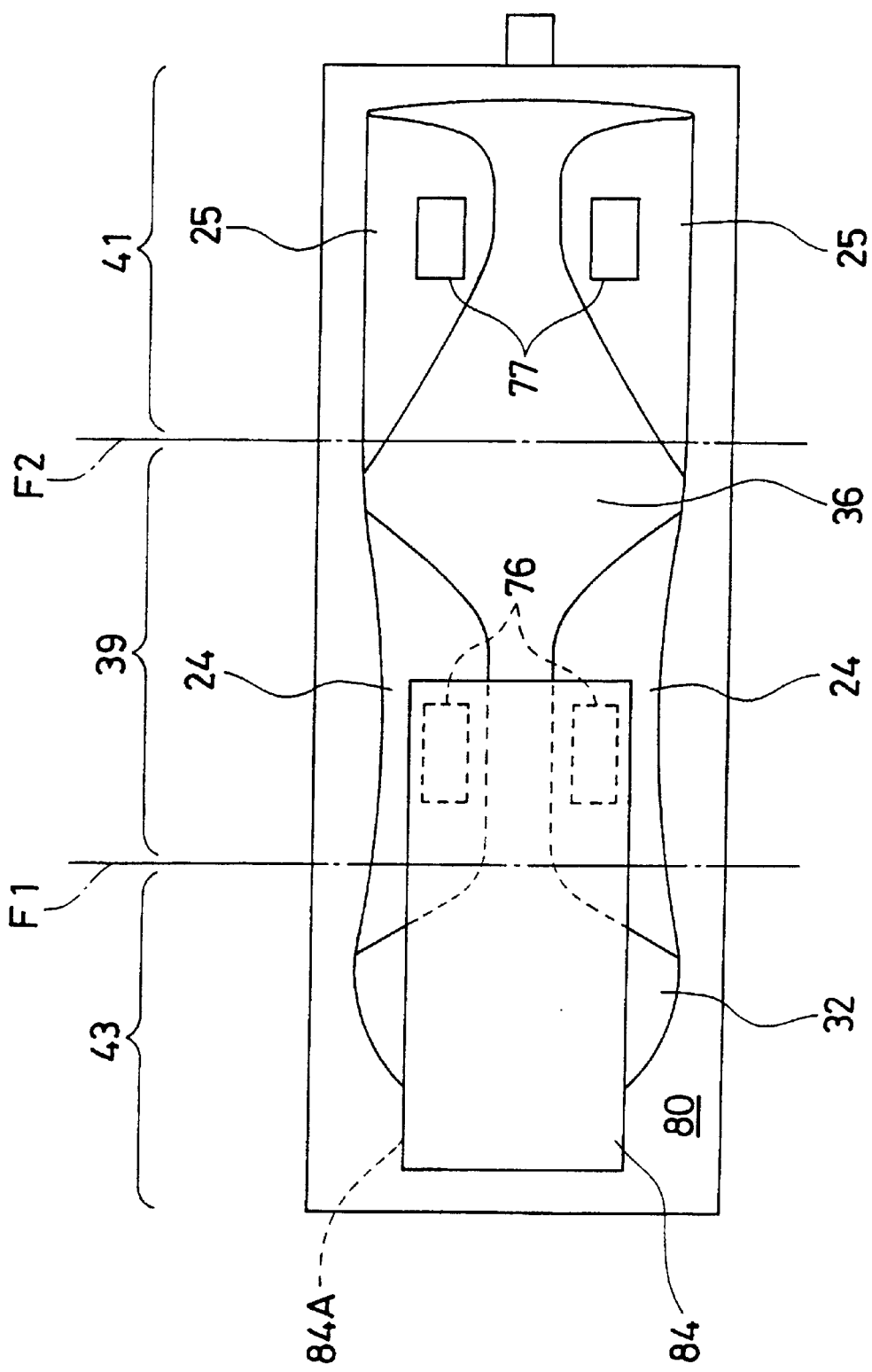
FIG. 11 is a top plan view of an alternative embodiment wrapper of the present invention with sanitary napkin placed thereon in substantially the same configuration as FIG. 2.

Various alternative embodiments of the present invention are possible. For example in the embodiment shown in FIG. 11, instead of only extending over part of the third section 32 of the main body portion 22 (i.e., the third region 43), the first flap adhesive cover 84 could be made longer so that it extends from one of the longitudinal ends of the main wrapper sheet 80 to overlie the first section 36 of the main body portion 22 (i.e., the first region 39) so that it covers the first flap adhesives 76 when the wrapper 78 and sanitary napkin 20 are in an unfolded condition. In this embodiment, the non-stick side 84A of the first flap adhesive cover 84 will face inward toward the main wrapper sheet 80, and the objectives of the invention will be accomplished regardless of the subsequent folded configuration of the wrapper 78 and napkin 20. Consequently, the wrapper 78 and sanitary napkin 20 could be folded upon themselves about the axes F1 and F2, or in any other manner, to provide the individually packaged absorbent article of the present invention.

Figure 7:
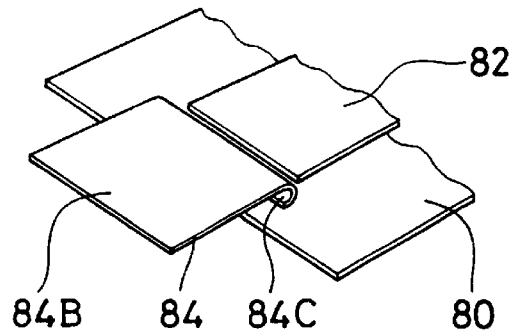
FIG. 7 is a fragmented perspective view of the wrapper shown in FIG. 6 with the free end of the flap release element folded back away from the main wrapper sheet.

The various embodiments of the wrapper 78 described herein can be made in any suitable manner. The flap adhesive covers 84 and 85 may be made of the same material as the main wrapper sheet or any adhesive cover material known in the art. The flap adhesive covers 84 and 85, if separate elements, can be joined to the main wrapper sheet 80 at any time during the manufacture of the individually packaged sanitary napkin 20 of the present invention. Preferably, for ease of manufacture, the first flap adhesive cover 84 will be joined to the main wrapper sheet 80 after the sanitary napkin 20 is already placed on the main wrapper sheet 80. This will eliminate the need to fold the first flap adhesive cover 84 back as shown in FIG. 7 to allow the sanitary napkin 20 to be placed on the main wrapper sheet 80. The release paper or release coating 82 on the main wrapper sheet 80, the non-stick surface 84A on the first flap adhesive cover 84 and the non-stick surface 85A on the second flap adhesive cover 85 can be applied either before or after the flap adhesive covers 84 and 85 are joined to the main wrapper sheet 80. Preferably, for ease of manufacture, these items are applied before the flap adhesive covers 84 and 85 are joined to the main wrapper sheet 80.

Figure 12:
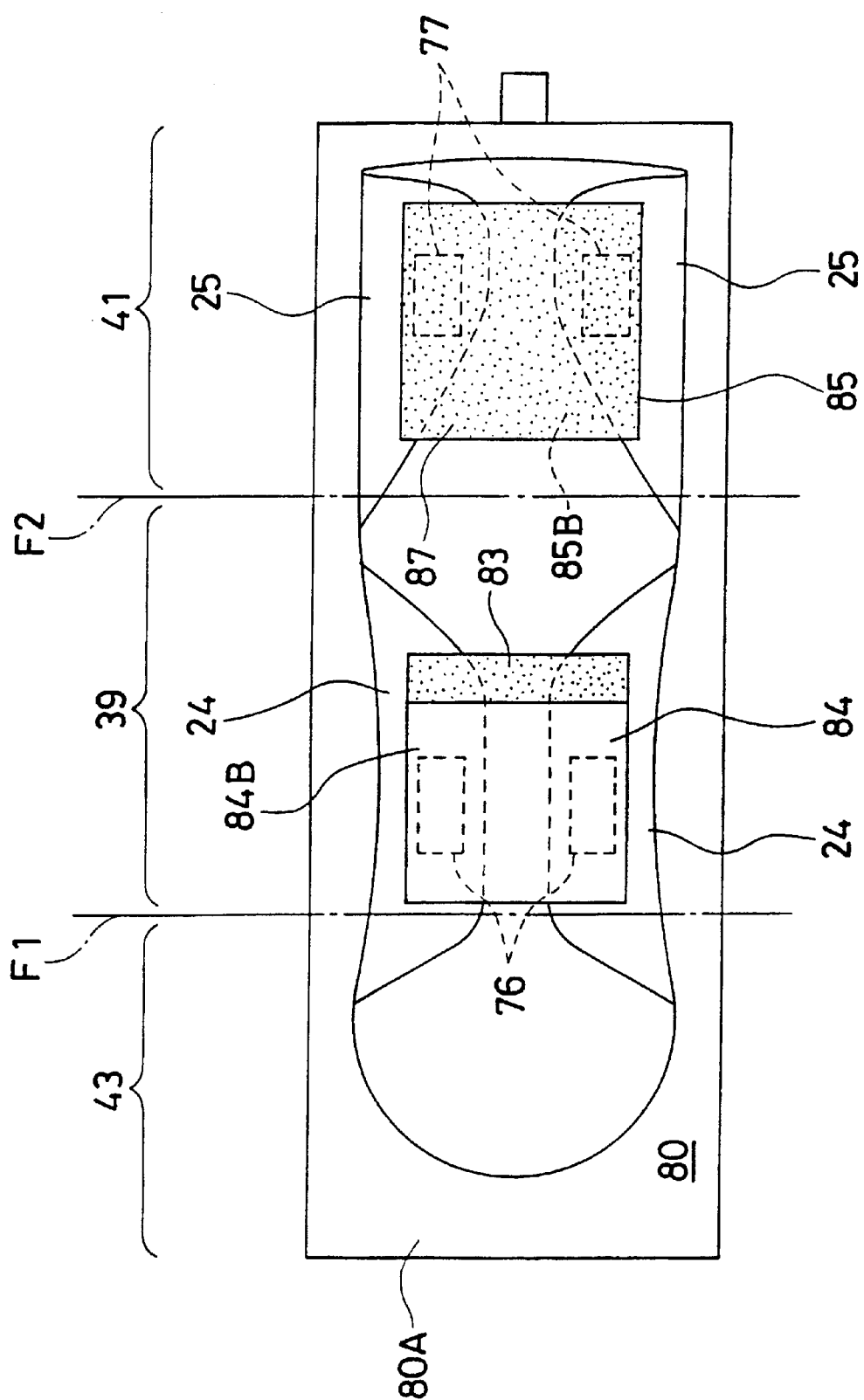
FIG. 12 is a top plan view of an alternative embodiment wrapper of the present invention with a sanitary napkin placed thereon in substantially the same configuration as FIG. 2.

More preferably, for ease of manufacture, the first flap adhesive cover 84 and the second flap adhesive cover 85 may be placed onto the first flaps 24 and the second flaps respectively as shown in FIG. 12 before the flap adhesive covers 84 and 85 are joined to the main wrapper sheet 80. The non-stick surface 84A covers the first flap adhesives 76 and the non-stick surface 85A covers the second flap adhesives 77. The opposing sides 84B and 85B which are not treated releasably may be provided with the adhesive layers 83 and 87 respectively either before or after the flap adhesive covers 84 and 85 are placed onto the flaps 24 and 25. Then the third region 43 is folded toward the first region 39, and the adhesive layer 83 applied to the first flap adhesive cover 84 is undetachably joined to the first end portion 80A of the main wrapper sheet 80. After that, the second region 41 is folded toward the outer surface 80E of the main wrapper sheet 80 in the third region 43 as shown in FIG. 9, and the adhesive layer 87 applied to the second flap adhesive cover 85 is undetachably joined to the outer surface 80E of the main wrapper sheet 80. When the individual packaged sanitary napkin 20 is opened, the first flap adhesive cover 84 is removed from the first flaps 24 but it stays with the first end portion 80A of the main wrapper sheet 80. The second flap adhesive cover 85 is also removed from the second flaps 25 but it stays with the outer surface 80E of the main wrapper sheet 80.

Figure 13:
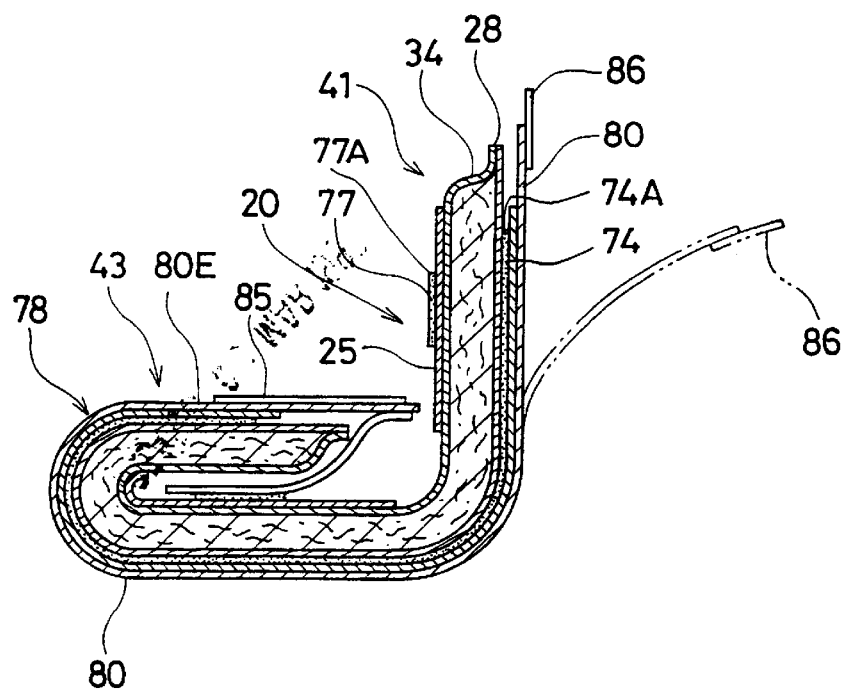
FIG. 13 is a first cross-sectional view (taken along the longitudinal centerline) of the present invention explaining an action of removing a wrapper from a sanitary napkin.
Figure 14:
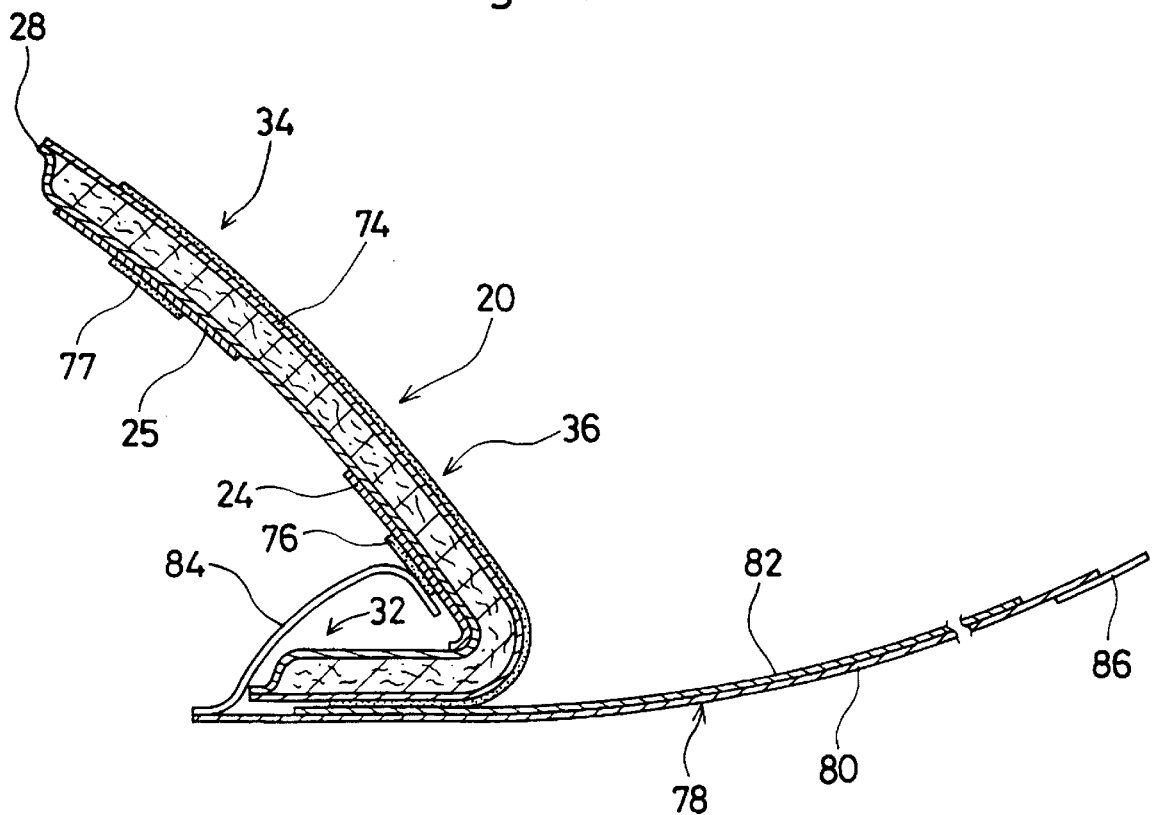
FIG. 14 is a second cross-sectional view (taken along the longitudinal centerline) of the present invention explaining an action of removing a wrapper from a sanitary napkin.

The consumer will ordinarily carry the individually packaged sanitary napkin of the present invention in the form depicted in FIGS. 9 and 10. As shown in FIG. 13, the individually packaged sanitary napkin of the present invention may be opened by peeling the tape tab 86 from the wrapper 78 and breaking the frangible seals along the longitudinal side edges 80D of the main wrapper sheet 80. The second flap adhesives 77 is separated from the second flap adhesive cover 85 and exposed. The second flap adhesive cover 85 remains the outer surface 80E of the main wrapper sheet 80. This gives the consumer access to the end edge 28 of the main body portion 22 of the second region 41. The consumer may then take hold of the end edge 28 of the main body portion 22 of the second region 41 and pull the tape tab 86 from the sanitary napkin 20 as shown in FIG. 13. As the sanitary napkin 20 is separated from the wrapper 78, the central pad adhesive 74 is separated from the release paper 82. When the first section 36 and the second section 34 of the main body portion 22 separate from the wrapper 78, the first flap adhesive cover 84 begins to separate from the first flap adhesives 76 provided on the first flaps 24 as shown in FIG. 14. The sanitary napkin 20 is further pulled from the wrapper 78, the sanitary napkin 20 and the wrapper 78 are separated from one another. The separation of the sanitary napkin 20 from the wrapper 78 is preferably achieved in a single motion.

In the preferred embodiment described above, when the second region 41 is separated from the third region 43 (i.e., when the second adhesive 77 is separated from the second flap adhesive cover 85), the second flap adhesive cover 85 will not move with the second flap adhesive 77 and will not separate from the outer surface 80E because the edge 87A (refer to FIGS. 5 and 9) of the adhesive layer 87 extends adjacent to the second end portion 80B of the main wrapper sheet 80 beyond the edge 77A of the second flap adhesive 77 at a distance T. In addition, because the edge 74A of the central pad adhesive 74 in the third region 41 extends adjacent to the end edge 28 of the main body portion 22 beyond the edge 77A of the second flap adhesive 77 at a distance S, the end edge 28 of the second section 36 will move with the main wrapper sheet 80 and then the second flap adhesive 77 will separate from the second flap adhesive cover 85. Such a structure provides give the consumer easy operation to peel the second region 41 from the third region 43.

Once the sanitary napkin is removed from the wrapper 78 and installed in the wearer's panties, the consumer may fold the wrapper 78, secure the wrapper 78 in its folded orientation by reattaching resealable tape tab 80 to wrapper 78. The consumer may then store the folded wrapper 78 for rewrapping and disposing of the used sanitary napkin. The wearer need not worry about collecting and disposing of loose flap adhesive release strips, that were previously required, since all release strips are attached to or integral with the wrapper 78. The present invention, therefore, provides the wearer with a clean sanitary napkin 20 which is easily installed and without extra pieces of waste which must be collected.

The disclosures of all patents, patent applications (and any patents which issue thereon, as well as any corresponding published foreign patent application), and publications mentioned throughout this description are hereby incorporated by reference herein. It is expressly not admitted, however, that any of the documents incorporated by reference herein teach or disclose the present invention.

It is to be recognized that the foregoing detailed description of the preferred embodiment of the present invention is given merely by way of illustration, and that numerous modifications and variations may become apparent to those skilled in the art without departing from the spirit and scope of the invention. Therefore, the scope of the present invention is to be determined by reference to the appended claims.

What is claimed is:

1. An individually packaged absorbent article comprising:
   (a) an absorbent article extending in a longitudinal direction and comprising a main body portion having a pair of longitudinal side edges, a pair of end edges, a garment surface, and a body surface, wherein the garment surface of the main body portion may be placed in a wearer's undergarment, and the absorbent article comprises a pair of first flaps joined to the main body portion and extending laterally outward beyond a longitudinal side edge of the main body portion and a pair of second flaps joined to the main body portion apart from the first flaps in the longitudinal direction and extending laterally outward beyond a longitudinal side edge of the main body portion, wherein the garment surface of each of the first and second flaps comprises a first flap fastener and a second flap fastener respectively, and the first and second flaps are folded over the body surface of the main body portion to expose the flap fasteners;

(b) a wrapper for the absorbent article, the wrapper comprising a main wrapper sheet and a first flap fastener cover, wherein (c) the main wrapper sheet comprising a pair of longitudinal side portions, a pair of end portions, an inner surface facing the main body portion and an outer surface, the main wrapper sheet is positioned adjacent to the garment surface of the main body portion, wherein the main wrapper sheet and the main body portion of the absorbent article comprises at least two transverse axes and at least three regions divided by the two axes, wherein the three regions comprise a first region into which a majority of the first flaps extends, a second region into which a majority of the second flaps extends and a third region, (d) the first flap fastener cover is joined to at least a part of the main wrapper sheet of the third region, wherein (e) the main wrapper sheet and the main body portion of the absorbent article are folded as a unit about one axis of the two axes so that the majority of the first flaps faces the main body portion of the third region, and the first flap fastener cover is releasably affixed to the first flap fasteners, and (f) the main wrapper sheet and the main body portion of the absorbent article are folded as a unit about the other axis of the two axes so that the majority of the second flaps faces the outer surface of the main wrapper sheet, and the second flap fasteners of the second flaps are releasably affixed to the outer surface of the main wrapper sheet.

2. The absorbent article of claim 1 wherein the absorbent article further comprises a second flap fastener cover releasably affixed to the second flap fastener of the second flaps, wherein the second flap fastener cover is joined to the outer surface of the main wrapper sheet.

3. The absorbent article of claim 2 wherein the first flap fastener cover comprises a separate element joined to the wrapper sheet, and the second flap fastener cover comprises a separate element joined to the main wrapper sheet.

4. The absorbent article of claim 1 wherein the first region is positioned between the second region and the third region, the third region is folded onto the main body portion of the first region so that the main wrapper sheet faces outside, and the second region is folded onto the main wrapper sheet of the third region.

5. The absorbent article of claim 4 wherein the longitudinal edge portions of the main wrapper sheet extend beyond the longitudinal side edges of the main body portion of the absorbent article, at least one end portion of the main wrapper sheet of the third region extends beyond the end edge of the main body portion of the third region, and the first flap fastener cover of the first flap fastener is joined to the end portion of the main wrapper sheet of the third region.

6. The absorbent article of claim 1 wherein the absorbent article further comprises a main body portion fastener which is disposed on the garment surface of the main body portion and extends in the longitudinal direction, wherein the main body portion fastener extends adjacent to the end edge of the main body portion beyond the second flap fastener of the second flaps.

7. The absorbent article of claim 2 wherein the first region is positioned between the second region and the third region, wherein the third region is folded onto the main body portion of the first region so that the main wrapper sheet faces outside, and the second region is folded onto the third region so that the second flap fastener cover faces the outer surface of the main wrapper sheet of the third region.

8. The absorbent article of claim 7 wherein the second flap fastener cover is joined to the outer surface of the main wrapper sheet of the third region at least at a point adjacent to the end portion of the main wrapper sheet of the second region beyond the second flap fastener of the second flaps.

9. The absorbent article of claim 8 wherein the absorbent article further comprises a main body portion fastener which is disposed on the garment surface of the main body portion and extends in the longitudinal direction, wherein the main body portion fastener extends adjacent to the end edge of the main body portion beyond the second flap fastener of the second flaps.

10. The absorbent article of claim 1 wherein the main wrapper sheet and the flap fastener covers can be removed from both the main body portion of the absorbent article and the flaps in a single motion.

* * * * *